US00PP30222P3

(12) United States Plant Patent
Bornstein

(10) Patent No.: US PP30,222 P3
(45) Date of Patent: Feb. 19, 2019

(54) ***GYPSOPHILA* PLANT NAMED 'PEARLS GRANDTASTIC'**

(50) Latin Name: ***Gypsophila paniculata* L.**
Varietal Denomination: Pearls Grandtastic

(71) Applicant: Selecta Cut Flowers S.A.U., Barcelona (ES)

(72) Inventor: Menachem Bornstein, Holon (IL)

(73) Assignee: Selecta Cut Flowers S.A.U., Barcelona (ES)

( * ) Notice: Subject to any disclaimer, the term of this patent is extended or adjusted under 35 U.S.C. 154(b) by 0 days.

(21) Appl. No.: 15/731,602

(22) Filed: Jul. 6, 2017

(65) Prior Publication Data

US 2019/0014708 P1 Jan. 10, 2019

(51) Int. Cl.
*A01H 5/02* (2018.01)
*A01H 6/00* (2018.01)

(52) U.S. Cl.
USPC ..... Plt./354
CPC ..... *A01H 6/00* (2018.05); *A01H 5/02* (2013.01)

(58) Field of Classification Search
USPC ..... Plt./354
See application file for complete search history.

*Primary Examiner* — Keith O. Robinson
(74) *Attorney, Agent, or Firm* — Barbara Campbell; Cochran Freund & Young LLC

(57) ABSTRACT

A new *Gypsophila* plant particularly distinguished by very large, double flowers and an upright growth habit, is disclosed.

1 Drawing Sheet

Genus and species: *Gypsophila paniculata* L.
Variety denomination: 'Pearls Grandtastic'.

CROSS-REFERENCE TO RELATED APPLICATIONS

An application with the Community Plant Variety Rights Office was filed on Apr. 4, 2017. 'Pearls Grandtastic' has not been made publicly available or sold more than one year prior to the filing date of the instant application.

BACKGROUND OF THE NEW PLANT

The present invention comprises a new and distinct variety of *Gypsophila*, botanically known as *Gypsophila paniculata* L., and hereinafter referred to by the variety name 'Pearls Grandtastic'. 'Pearls Grandtastic' originated from an open-pollination conducted in Negev, Israel in April 2010 between the proprietary female *Gypsophila* variety 'BL-MD-F-56' (unpatented) and an unnamed and unpatented male *Gypsophila* variety.

The seeds from the cross were sown and plants were grown for evaluation, where an individual plant designated 'Pearls Grandtastic' was selected from the group of plants in Negev, Israel in August 2010.

In September 2010, 'Pearls Grandtastic' was first vegetatively propagated by side branch cuttings. 'Pearls Grandtastic' was found to reproduce true to type in successive generations of asexual propagation via side branch cuttings.

SUMMARY

The following are the most outstanding and distinguishing characteristics of this new variety when grown under normal horticultural practices in Negev, Israel.

1. Very large, double flowers; and
2. An upright growth habit.

DESCRIPTION OF THE PHOTOGRAPH

This new *Gypsophila* plant is illustrated by the accompanying photograph which shows the plant's overall plant habit including form and flowers. The photograph is of a 22-week-old plant grown outdoors in Colombia in April 2016. The colors shown are as true as can be reasonably obtained by conventional photographic procedures.

DESCRIPTION OF THE NEW VARIETY

The following detailed descriptions set forth the distinctive characteristics of 'Pearls Grandtastic'. The data which define these characteristics were collected from asexual reproductions carried out in Juja, Kenya. Data was collected on 20-week-old plants grown outdoors in Juja, Kenya in September 2016. Color references are to The R.H.S. Colour Chart of The Royal Horticultural Society of London (R.H.S.) 2007.

Classification:
- *Family.*—Caryophyllaceae.
- *Botanical.*—*Gypsophila paniculata* L.
- *Common.*—Baby's breath.
- *Designation.*—'Pearls Grandtastic'.

Parentage:
- *Female parent.*—The proprietary female *Gypsophila* variety 'BL-MD-F-56' (unpatented).
- *Male parent.*—An unnamed and unpatented male *Gypsophila* variety.

Plant:
- *Form.*—Perennial, shrub type.
- *Growth habit.*—Upright.
- *Height.*—110.0 cm.
- *Width.*—90.0 cm.
- *Time to produce a finished flowering plant.*—15 to 20 weeks; 3 to 4 weeks for rooting with 11 to 14 weeks between planting and flowering, depending on weather and cultivation conditions.
- *Propagation type.*—Vegetative, by side branch cuttings.

*Time to initiate and develop roots.*—2 weeks, fully rooted and ready for planting after 3 to 4 weeks.

*Root description.*—White to light brown, RHS 155A at root tip and RHS 162D at the base; woody main spike with branched fibrillary secondary roots.

Flowering stems:

*Number of branches per plant.*—6 to 9.

*Basal branching.*—Present.

*Stem strength.*—Stable.

*General description.*—Panicle.

*Length.*—90.0 cm.

*Diameter.*—0.6 cm to 0.8 cm at the stem base.

*Internode length.*—5.0 cm to 6.0 cm at the stem base.

*Color.*—RHS 147C (Yellow-Green).

*Texture.*—Glabrous.

Leaves:

*Arrangement.*—Opposite.

*Shape.*—Lanceolate.

*Cross section of leaf.*—Moderately concave.

*Apex.*—Acute.

*Base.*—Cuneate.

*Margin.*—Entire.

*Immature and mature leaf color.*—Upper surface: RHS 137A. Lower surface: RHS 137B.

*Length.*—6.5 cm to 7.5 cm.

*Width.*—1.2 cm to 1.4 cm.

*Texture.*—Fine pubescence on both surfaces; more fine on the upper surface than on the lower surface.

*Venation type.*—Parallel.

*Venation color.*—Upper surface: RHS 137A. Lower surface: RHS 137B.

Inflorescence:

*Inflorescence type.*—Compound cymes with numerous flowers; panicles.

*Flowering season.*—Year-round; 12 hours and above light duration.

*Lastingness of individual flowers on the plant.*—10 to 12 days.

*Lastingness of the flowers as a cut flower.*—10 to 12 days.

*Flower width.*—1.0 cm to 1.2 cm.

*Flower depth.*—0.7 cm to 0.8 cm.

*Flower shape.*—Oblate consisting of many double-type petals.

*Flower profile, upper part.*—Moderately convex.

*Fragrance.*—Faint, unpleasant smell.

*Number of inflorescences per plant.*—6 to 9.

*Number of flowers per inflorescence.*—Average between 600 and 900.

*Inflorescence pubescence.*—Absent.

*Flower buds.*—Color: RHS 155 (White). Shape: Oblate. Length: 0.45 cm. Diameter: 0.3 cm.

*Peduncle.*—Length (height): 90.0 cm. Diameter: 50.0 cm. Strength: Stable. Texture: Glabrous. Color: RHS 138B.

*Pedicel.*—Length: 0.6 cm to 0.9 cm. Diameter: 0.1 cm. Strength: Stable. Texture: Fine. Color: RHS 137C.

*Petals.*—Arrangement: Pompon. Quantity: 45 to 52 per flower. Shape: Spatulate. Apex: Emarginate. Base: Cuneate. Margin: Entire. Curvature of longitudinal axis of petal: Moderately recurved. Size: Length: 0.45 cm. Width: 0.2 cm. Color: When opening (both upper and lower surfaces): RHS 155A. Fully opened (both upper and lower surfaces): RHS 155D. Surface texture (both upper and lower surfaces): Glabrous.

*Sepals.*—Arrangement: Like a cup. Quantity per flower: 5 to 7. Shape: Lanceolate. Apex: Acute. Base: Cuneate. Margin: Entire. Length: 0.35 cm. Width: 0.1 cm. Color (both upper and lower surfaces): RHS 147C (Yellow-Green). Surface texture (both upper and lower surfaces): Glabrous.

Reproductive organs:

*Stamens.*—None observed.

*Pistils.*—Quantity per flower: 1. Pistil length: 1.0 cm to 1.2 cm. Style length: 0.5 cm to 0.7 cm. Style color: RHS 181D. Stigma color: RHS 75D. Ovary color: RHS 137C.

Fruit and seed set: None observed.

Disease and pest/insect resistance: None observed.

COMPARISON WITH PARENTAL LINE AND KNOWN VARIETY

'Pearls Grandtastic' is distinguished from the female parent and the commercial comparison variety 'Million Star' (patent status unknown) as described in Table 1.

TABLE 1

Comparison with Parental Line and Commercial Variety

| Characteristic | 'Pearls Grandtastic' | Female parent 'BL-MD-F-56' | Commercial Variety 'Million Star' |
|---|---|---|---|
| Flower size | Very large | Large | Small |
| Flower type | Double | Double | Semi-double |

I claim:

1. A new and distinct variety of *Gypsophila* plant designated 'Pearls Grandtastic' as illustrated and described herein.

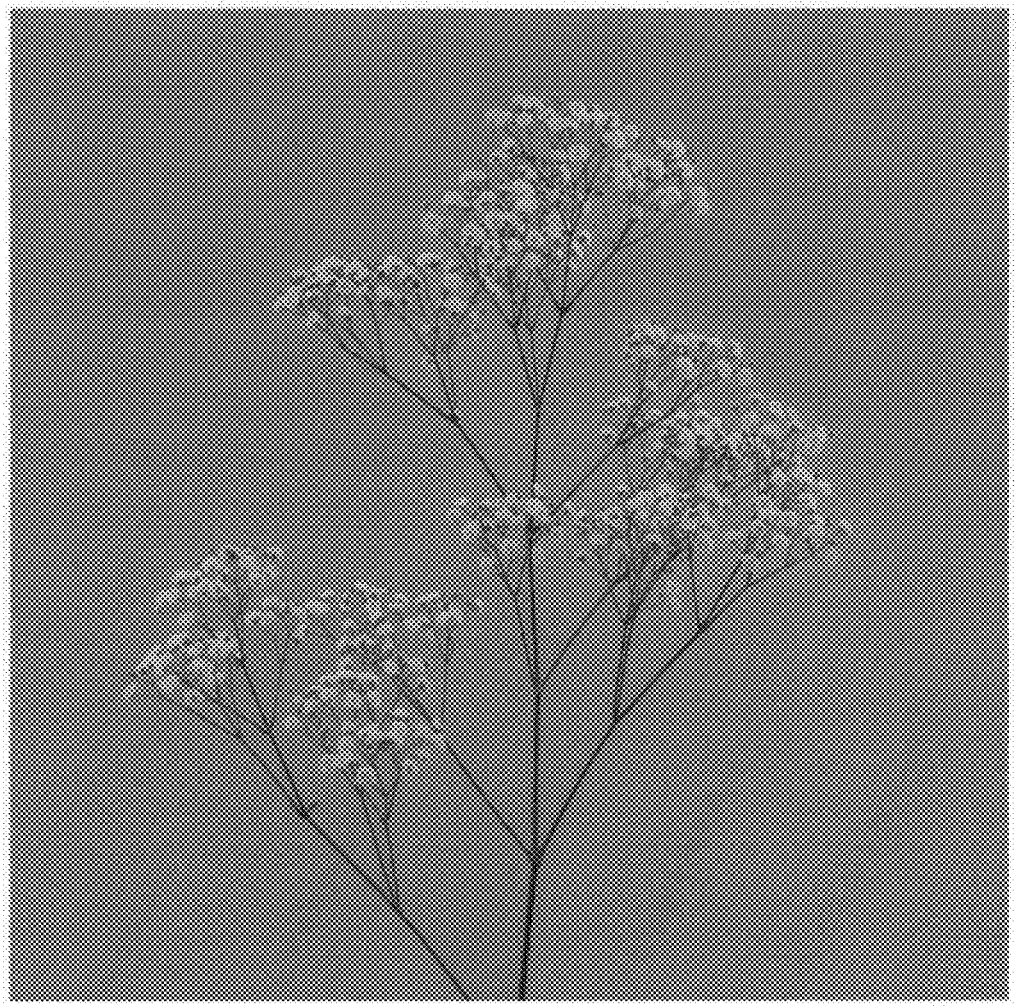

* * * * *